United States Patent
Wageneck et al.

(10) Patent No.: US 8,491,470 B1
(45) Date of Patent: Jul. 23, 2013

(54) SELF-EXAMINATION OTOSCOPE

(76) Inventors: Russell E. Wageneck, San Antonio, TX (US); Robert O. Wageneck, Santa Barbara, CA (US)

(*) Notice: Subject to any disclaimer, the term of this patent is extended or adjusted under 35 U.S.C. 154(b) by 0 days.

(21) Appl. No.: 13/317,710

(22) Filed: Oct. 27, 2011

(51) Int. Cl.
*A61B 1/227* (2006.01)

(52) U.S. Cl.
USPC .......................... 600/200; 600/189; 600/199

(58) Field of Classification Search
USPC ... 600/189, 199, 200; 351/223, 207; 359/482; 434/303
See application file for complete search history.

(56) References Cited

U.S. PATENT DOCUMENTS

| | | | | |
|---|---|---|---|---|
| 3,677,620 A * | 7/1972 | Bettencourt | ................ | 359/482 |
| 3,914,032 A * | 10/1975 | Takano et al. | ................ | 351/206 |
| 6,569,090 B1 * | 5/2003 | Mezzoli et al. | ................ | 600/200 |
| 7,802,909 B2 * | 9/2010 | Baker | ................ | 362/572 |

* cited by examiner

*Primary Examiner* — Todd Manahan
*Assistant Examiner* — Jessica Weiss
(74) *Attorney, Agent, or Firm* — Norman B. Rainer

(57) ABSTRACT

A viewing system associated with a conventional otoscope enables a person to examine the interior of his or her own ear. The viewing system utilizes a box-like enclosure containing a first mirror that reflects an image of the ear forwardly of the user's face, and a remote mirror that reflects the image back to the user's face.

5 Claims, 2 Drawing Sheets

SELF-EXAMINATION OTOSCOPE

BACKGROUND OF THE INVENTION

1. Field of the Invention

The present invention concerns an attachment for a commonplace otoscope which enables a person to examine an eardrum and external canal of either of his ears.

2. Description of the Prior Art

Otoscopes, as employed by physicians, are generally comprised of a housing having a forward extremity that tapers to a narrow speculum adapted to insert into a patient's ear, a light source, and a rear extremity having magnification means which enable the physician to see an enlarged view of illuminated portions of the ear.

Certain ear ailments are of a persistent nature, requiring frequent viewing of the ear to ascertain the effectiveness or progress of treatment. It would be inexpedient for the patient to visit his physician every day during the course of the ailment. Accordingly, it would be prudent for the patient to achieve some level of self-monitoring observation at home.

U.S. Pat. No. 5,501,652 to Woods discloses a self-examination otoscope which is specially constructed so that the rear extremity of the otoscope slidably accommodates a first telescoping tube which interacts with a second telescoping tube which enables the image of the illuminated ear to be viewed by the patient. Woods' device is expensive to construct because it requires the construction of a non-standard otoscope plus specialized fittings. Also, the Woods' device does not easily permit viewing by the physician.

It is accordingly an object of the present invention to provide an otoscope device which permits the user to view the eardrum and external canal of his own ear.

It is a further object of this invention to provide an otoscope device as in the foregoing object which permits a physician or other examiner to inspect the patient's eardrum and external ear canal.

It is an additional object of the present invention to provide a device of the aforesaid nature which represents an inexpensive viewing system associated with a conventional otoscope.

These objects and other objects and advantages of the invention will be apparent from the following description.

SUMMARY OF THE INVENTION

The above and other beneficial objects and advantages are accomplished in accordance with the present invention by the combination of an otoscope of conventional construction, and a viewing system associated with said otoscope:

Said otoscope is comprised of:
a) a housing having a forward portion that tapers upon a center axis to a narrow speculum adapted to enter a patient's ear, and a rear extremity having an associated lens to permit magnified viewing of the patient's ear,
b) a handle downwardly emergent from a bottom portion of said housing, and
c) a light source which illuminates the patient's ear.

Said viewing system is comprised of:
a) a box-like enclosure attached to the rear extremity of said otoscope housing and bounded in part by an upper panel having a first circular aperture, and a rear panel having a second aperture orthogonally centered upon said axis,
b) a mirror pivotably secured to a lower portion of said enclosure and adapted to be manually moved between a substantially horizontal lowermost position, and an uppermost position which intersects said axis at a 45° angle in a manner to permit external vision of said ear through said first aperture,
c) manipulating means exteriorly located from said enclosure and adapted to move said mirror between its two positions, and
d) an adjustable aiming mirror remote from said enclosure and permitting hand adjustment so as to cause the image of the patient's ear to enter one of his eyes.

In a preferred embodiment, a collimating tube is associated with said first aperture to provide an enhanced image of the ear undergoing examination.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
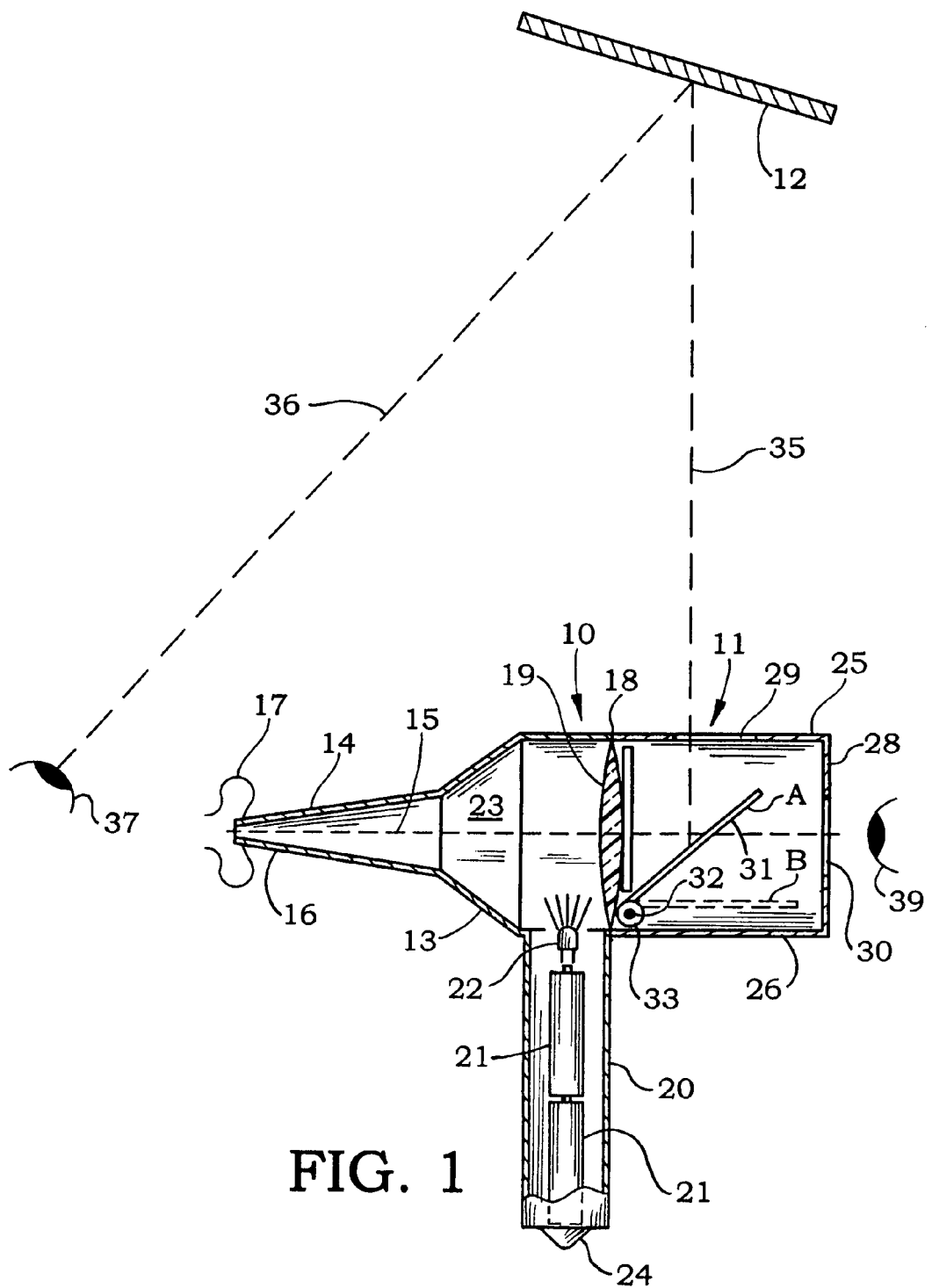
FIG. 1 is a sectional side view of an embodiment of the present invention.
Figure 2:
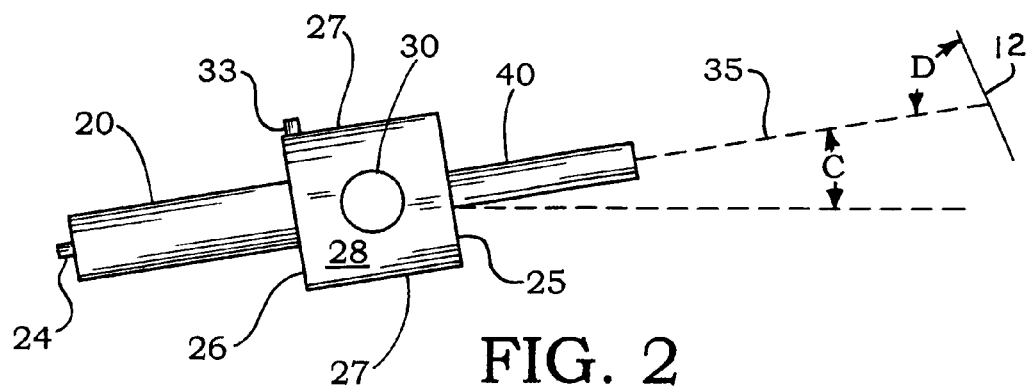
FIG. 2 is a rear view of the embodiment of FIG. 1 showing the otoscope at a proper angle for use.
Figure 3:
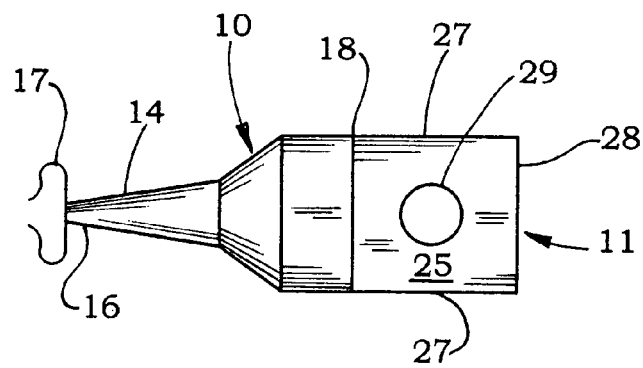
FIG. 3 is a fragmentary top view of the embodiment of FIG. 2.

Referring now to FIGS. 1-3, an embodiment of the self-examining otoscope system of the present invention is shown comprised of a commonplace, standard otoscope 10 and an interactive attachment 11 and remote mirror 12.

Said otoscope is comprised of a housing 13 having a forward portion 14 that tapers upon a center axis 15 to a narrow speculum end 16 adapted to enter the patient's ear 17. A rear extremity 18 of said housing contains a lens 19 to permit magnified viewing of the patient's ear. A handle 20 is downwardly directed from said housing, and contains batteries 21 which activate light bulb 22 in a manner to illuminate the interior 23 of said housing, passing light through said speculum, and into the patient's ear. An on/off switch 24 is positioned at the bottom of handle 20.

Attachment 11 is an enclosure attached to the rear extremity 18 of said housing and consisting of horizontal top and bottom panels 25 and 26, respectively, opposed side panels 27, and vertical rear panel 28. A first circular transmitting aperture 29 is centered in top panel 25, and a second circular transmitting aperture 30 is centered in rear panel 28. A flat first mirror 31 is mounted upon pivoting axle 32 within said enclosure. Turning knob 33 engages said axle exteriorly of said enclosure, and is adapted to rotate mirror 31 between a first position A which is at an angle of substantially 45° with respect to axis 15, and a second position B which is parallel to bottom panel 26.

In operation, the otoscope with attachment 11 is hand held by the user to insert speculum end 16 carefully into his ear. When first mirror 31 is in position A, light from the otoscope follows a first reflected light path emergent from said first aperture, as indicated by broken line 35, whereupon it contacts mirror 12, and is reflected upon second reflected light path 36 into the user's eye 37. In order that the reflected light is caused to directly enter the user's eye, it is necessary that otoscope be held so that the reflected light path 35 is between about 2° and 30° from horizontal, as shown by angle C in FIG. 2. Remote mirror 12 may be held by the user's other hand, thereby enabling light path 36 to directly enter the user's eye. Alternatively, said mirror can be adjustably mounted on a wall. Mirror 12 should be positioned at an angle D of 75° to 85° with respect to light path 35.

In an optional mode of use, first mirror 31 may be turned to its position B, which enables light from the otoscope to pass axially through transmitting aperture 30 into a physician's eye 39. Mirror 12 is positioned between 8 and 15 inches from the user's eye.

In a preferred embodiment, a collimating tube 40 is directly emergent from aperture 29 for the purpose of enhancing the image of the ear undergoing examination.

Figure 4:
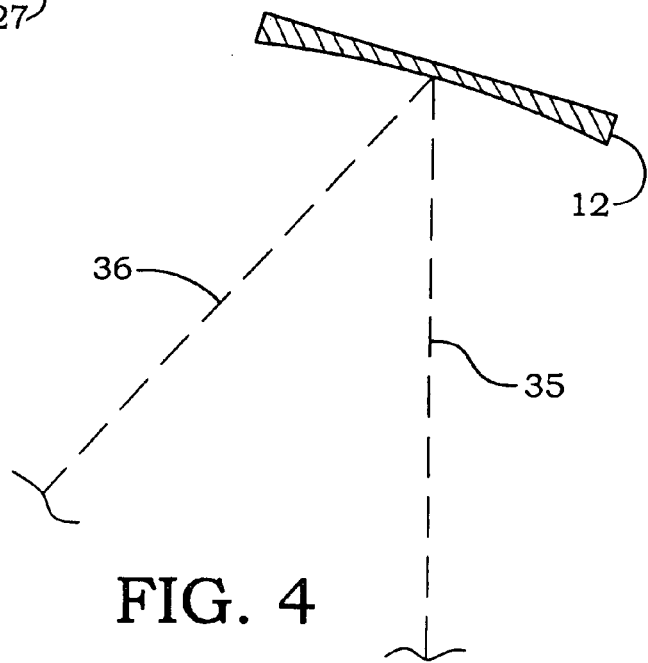
FIG. 4 is a fragmentary sectional top view of an alternative embodiment of the invention.

In an alternative embodiment, remote mirror 12 may be of circular concave configuration, as shown in FIG. 4, thereby magnifying the image seen by the user.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described our invention, what is claimed is:

1. A modified otoscope for enabling a person to examine the interior of his or her own ear, consisting essentially of:
    a) an otoscope unit comprised of a housing having a forward portion adapted to enter a person's ear, a rear extremity having a magnifying lens centered upon an axis aligned with said forward portion, and a handle downwardly directed from said housing and containing a light source,
    b) an enclosure rearwardly emergent from the rear extremity of said housing and bounded in part by a lower portion, an upper panel having a first circular aperture, and a rear panel having a second circular aperture centered upon said axis,
    c) a flat mirror located within said enclosure in pivotable securement to said lower portion and adapted to be manually moved between a lowermost position substantially parallel to said lower portion which permits light from said otoscope to emerge from said second aperture, and an uppermost position which intersects said axis at a substantially 45 angle in a manner to produce a first reflected light path through said first aperture, and
    d) manipulating means exteriorly located from said enclosure for moving said mirror between its two positions.

2. The modified otoscope of claim 1 wherein a collimating tube is associated with said first aperture and perpendicularly directed away from said housing.

3. A system for enabling self-examination of the interior of a person's ear and alternatively permitting examination by a physician, said system comprising:
    a) the modified otoscope of claim 1, and
    b) an aiming mirror positioned remotely from said otoscope so as to receive light from said first path and reflect said light upon a second path into one of said person's eyes.

4. The system of claim 3 wherein said aiming mirror has a circular concave configuration which produces a magnified image of the interior of the person's ear.

5. A method for enabling a person to inspect the interior of his or her own ear comprising:
    a) gripping in one hand the handle of the modified otoscope of claim 1,
    b) inserting said forward portion into the ear intended to be inspected while directing said upper panel forwardly of said person,
    c) holding said modified otoscope by said handle in manner such that a first reflected light path is angled upwardly between about 2 and 30 degrees from a horizontal plane and strikes a remote aiming mirror at a distance of 8 to 15 inches in front of the person's face in a manner to receive said first reflected light path at an angle of 75 to 85 degrees, and
    d) causing light to be reflected by said aiming mirror onto a second path which enters the person's eye.

* * * * *